United States Patent
Hakansson

(10) Patent No.: US 8,556,024 B2
(45) Date of Patent: Oct. 15, 2013

(54) DEVICE FOR HEARING PROTECTION

(75) Inventor: Jorgen Hakansson, Tyringe (SE)

(73) Assignee: SwedSafe AB, Höör (SE)

( * ) Notice: Subject to any disclaimer, the term of this patent is extended or adjusted under 35 U.S.C. 154(b) by 0 days.

(21) Appl. No.: 13/816,848

(22) PCT Filed: Aug. 4, 2011

(86) PCT No.: PCT/SE2011/050977
§ 371 (c)(1),
(2), (4) Date: Feb. 13, 2013

(87) PCT Pub. No.: WO2012/026864
PCT Pub. Date: Mar. 1, 2012

(65) Prior Publication Data
US 2013/0161121 A1 Jun. 27, 2013

(30) Foreign Application Priority Data

Aug. 26, 2010 (SE) .................................. 1050875-2

(51) Int. Cl.
*H04R 25/02* (2006.01)
*H04R 25/00* (2006.01)

(52) U.S. Cl.
USPC ............ 181/135; 181/130; 381/328; 381/329

(58) Field of Classification Search
USPC .......... 181/135, 130; 381/328, 329; D24/106; 128/864
See application file for complete search history.

(56) References Cited

U.S. PATENT DOCUMENTS

| | | | | |
|---|---|---|---|---|
| 5,074,375 | A * | 12/1991 | Grozil | 181/135 |
| D375,551 | S * | 11/1996 | Esler et al. | D24/106 |
| 6,695,093 | B1 | 2/2004 | Falco | |
| 7,464,786 | B2 * | 12/2008 | Falco et al. | 181/135 |
| 7,743,771 | B2 | 6/2010 | Falco | |
| 8,413,663 | B2 * | 4/2013 | Turdjian et al. | 128/864 |
| 2007/0102006 | A1 * | 5/2007 | Falco | 128/864 |
| 2007/0102007 | A1 * | 5/2007 | Falco | 128/864 |
| 2008/0181441 | A1 | 7/2008 | Smith | |

OTHER PUBLICATIONS

International Search Report from corresponding International Application No. PCT/SE2011/050977, mailed on Nov. 29, 2011.

* cited by examiner

*Primary Examiner* — Edgardo San Martin
(74) *Attorney, Agent, or Firm* — Renner, Otto, Boisselle & Sklar, LLP

(57) ABSTRACT

A device (10) for hearing protection, comprising an elongated stem (11) and a grip part (12), wherein the stem (11) comprises a connecting portion (14) for connection with the grip part (12), an attachment portion (15) for attachment to an earplug (13) projecting radially to the stem (11) and being arranged for insertion into an ear canal (25), and an intermediate portion (16) arranged between the connecting portion (14) and the attachment portion (15). The stem (11) comprises a first curve (21) arranged between the connecting portion (14) and the intermediate portion (16) and a second curve (22) arranged between the attachment portion (15) and the intermediate portion (16), wherein the intermediate portion (16) is arranged in a first angle (β) to the connecting portion (14) and a second angle (γ) to the attachment portion (15).

Figure 1:
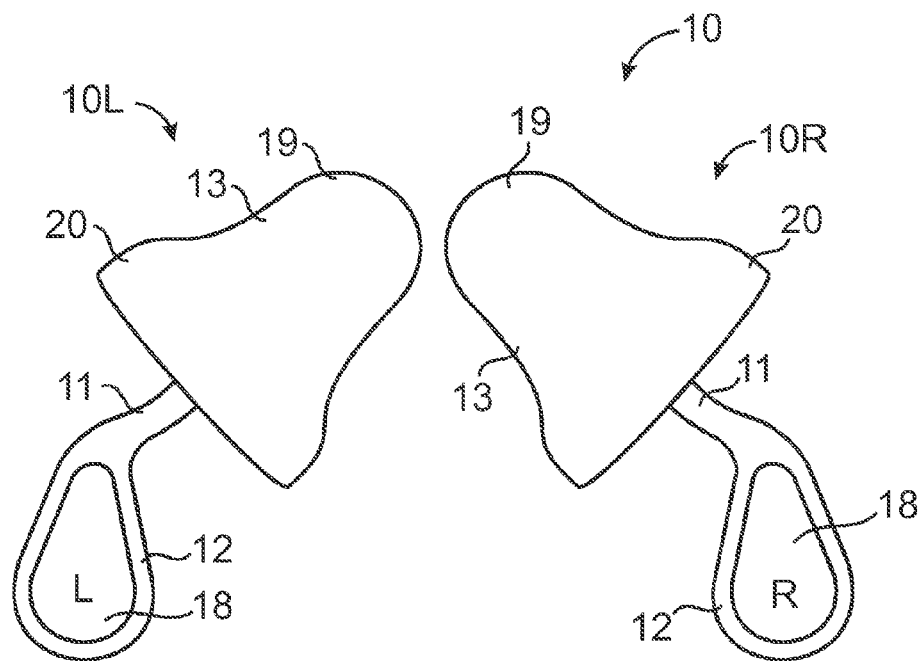

11 Claims, 6 Drawing Sheets

DEVICE FOR HEARING PROTECTION

FIELD OF THE INVENTION

The invention relates to a device for hearing protection. More specifically, the present invention relates to a device for hearing protection comprising an elongated stem for connection to an earplug projecting radially to the stem and being arranged for insertion in an ear canal. One common type of earplug is a foam plug or similar. Earplugs of different types of flexible plastic and rubber materials are also used. The earplug can be fixed or removably connectable to the stem. This type of devices for hearing protection are generally used to protect auditory organs of a user being in environments of sound being harmful for the hearing, such as within industry having noisy environments or other environments with harmful sound.

PRIOR ART

There are several different types of devices for hearing protection comprising a stem and an earplug in the prior art. One such type of device is for example disclosed in WO200851516. The device disclosed in WO200851516 comprises a stem and a grip part arranged at an angle to the stem, so that the grip part is inclined downward in relation to the stem. The stem is arranged with a flange for interaction with an earplug, so that the earplug can be connected to the stem. The grip part can be somewhat flattened for easier gripping by a person.

A problem with such devices for hearing protection according to prior art is that it can be difficult to position the earplug in the ear canal correctly.

A drawback of such prior art devices is that the protection against harmful sound can be insufficient.

Another problem with such prior art devices is that they can result in discomfort during use.

SUMMARY OF THE INVENTION

An object of the present invention is to avoid the drawbacks and problems of the prior art. The device according to the invention results in simple, comfortable and safe positioning of the earplug in the ear canal, which provides an improved protection against harmful sound.

The present invention relates to a device for hearing protection, comprising an elongated stem and a grip part, wherein the stem comprises a connecting portion for connection with the grip part, an attachment portion for attachment to an earplug projecting radially to the stem and being arranged for insertion into an ear canal, and an intermediate portion arranged between the connecting portion and the attachment portion, characterised in that the stem comprises a first curve arranged between the connecting portion and the intermediate portion and a second curve arranged between the attachment portion and the intermediate portion, wherein the intermediate portion is arranged in a first angle to the connecting portion and a second angle to the attachment portion, so that the intermediate portion is inclined backwards in relation to the attachment portion when the attachment portion is attached to an earplug arranged in an ear canal. The form of the stem results in an easier insertion of the earplug passed tragus and passed a curvature of the ear canal, wherein the earplug easier can be positioned in a comfortable and safe position.

The stem can be arranged in an angle to the grip part, so that the stem projects obliquely upwards from the grip part when the attachment portion is attached to an earplug arranged in an ear canal. Consequently, the device is formed according to a normal ear canal to further facilitate the insertion of the earplug therein.

The stem can be detachably connectable or fixed to an earplug. The earplug can be oval or formed with elliptic cross section. It has been shown that a normal ear canal has a somewhat oval or elliptic cross section, so that the ear canal is somewhat elongated in substantially vertical direction. By an oval earplug is provided a safe and comfortable hearing protection. The earplug can be detachably connectable to the stem and thereby replaceable.

The grip part can be formed as a plate, wherein the grip part extends substantially in a first plane. Hence, a safe grip for a user is provided, wherein the device easily can be handled. A long axis of the elliptic cross section of the earplug can extend in a direction corresponding to the grip part, wherein both of the long axis of the earplug and the grip part extend in substantially vertical planes during use of the device. Hence, the oval structure or elliptic direction of the earplug corresponds to the oval structure of the ear canal when a user is holding the grip part between his thumb and index finger, wherein the oval structure of the earplug is positioned correctly in relation to the oval structure of the ear canal during insertion of the earplug in the ear canal. Thus, during insertion of the earplug a user can hold the grip part in a way so that the grip part is directed downwards, wherein the oval shape of the earplug is positioned correctly in relation to the oval shape of the ear canal. When the earplug is positioned in the ear canal the grip part extends substantially downward in a vertical direction, wherein a user knows that the positioning of the device and the earplug is correct and that the earplug is inserted correctly.

The attachment portion can be elliptic and the earplug can be arranged with a recess for receiving the attachment portion. Hence, the positioning of the earplug on the stem is ensured, so that the oval structure of the earplug is positioned correctly. Simultaneously, turning of the earplug around the centre axis of the attachment portion is prevented. The attachment portion can be provided with at least one and suitably two or more radially projecting projections for interaction with the earplug, so that the earplug not unintentionally is removed from the stem and so that turning of the earplug is prevented.

Further characteristics and advantages of the present invention will become apparent from the description of the embodiments below, the appended drawings and the dependent claims.

SHORT DESCRIPTION OF THE DRAWINGS

Figure 2:
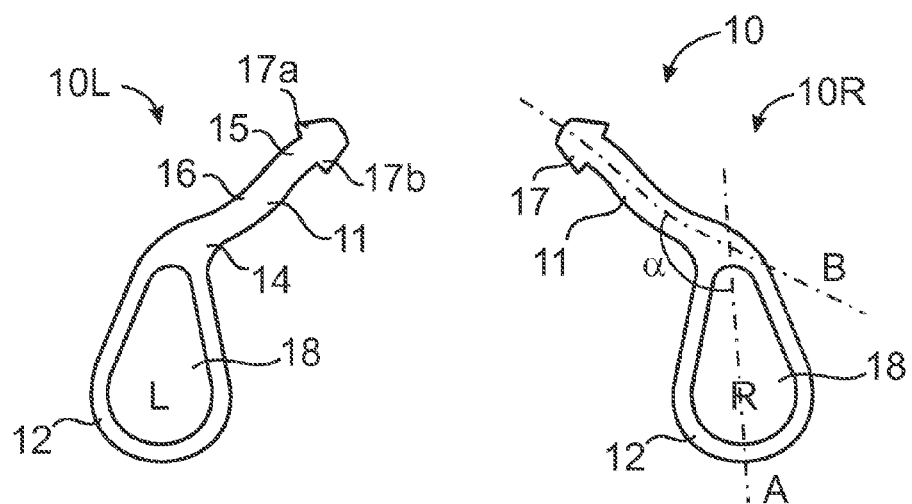
Figure 3:
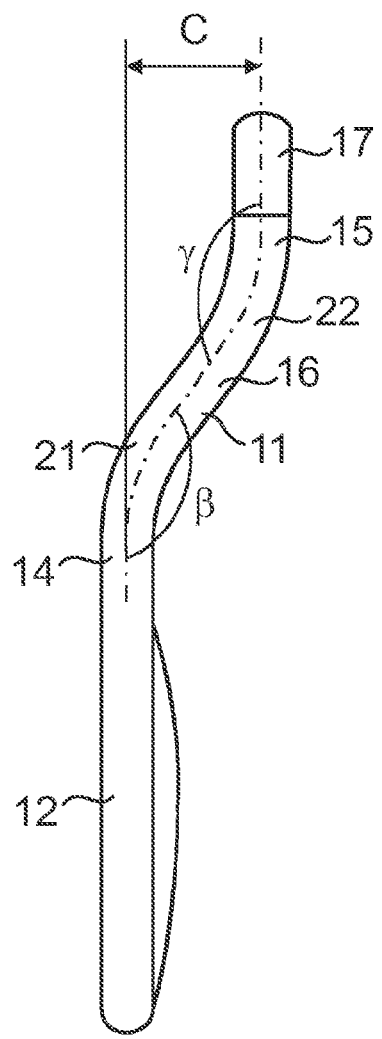
Figure 4:
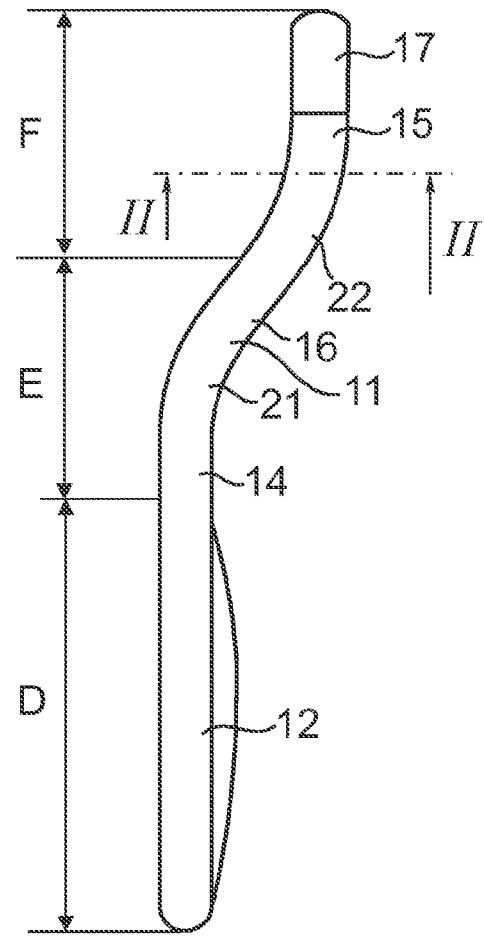
Figure 5:
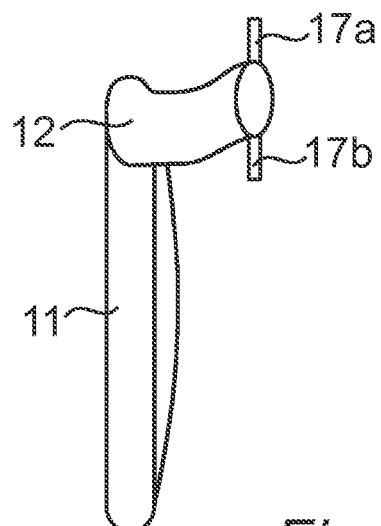
Figure 6:
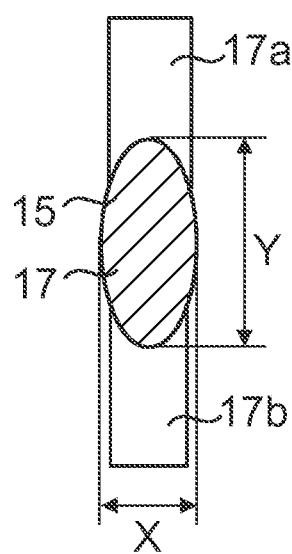
Figure 7:
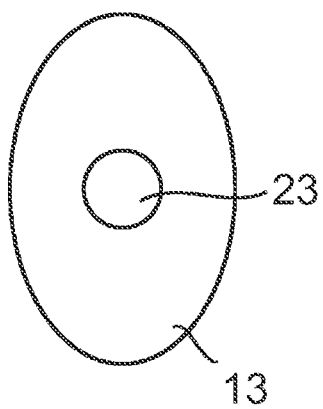
Figure 8:
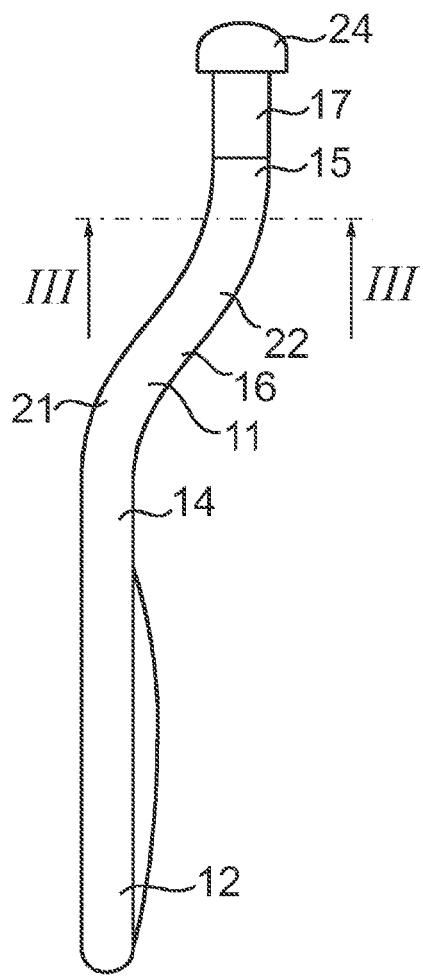
Figure 9:
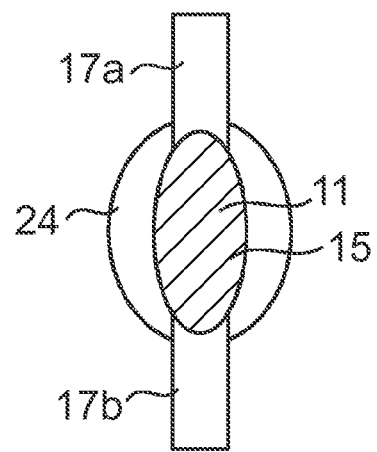
Figure 10:
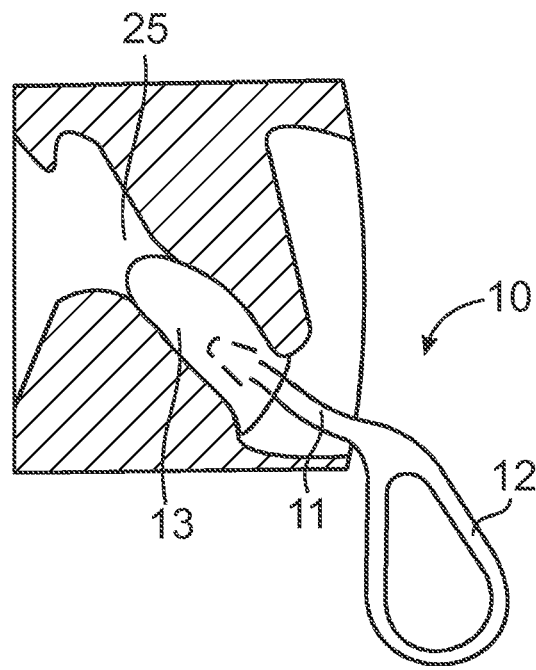
Figure 11:
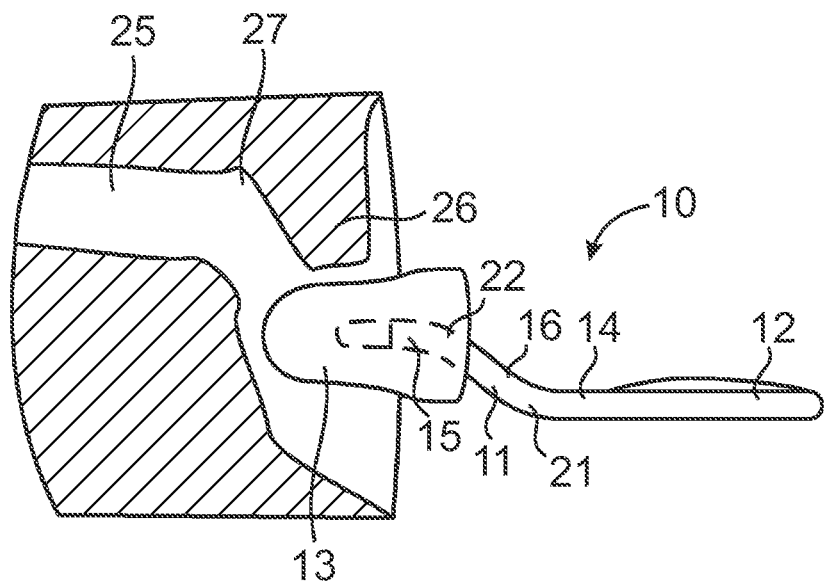
Figure 12:
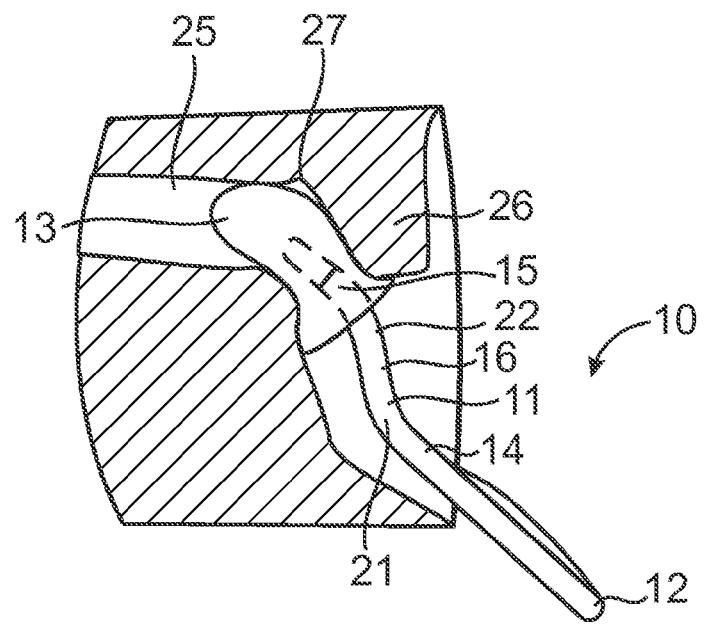
Figure 13:
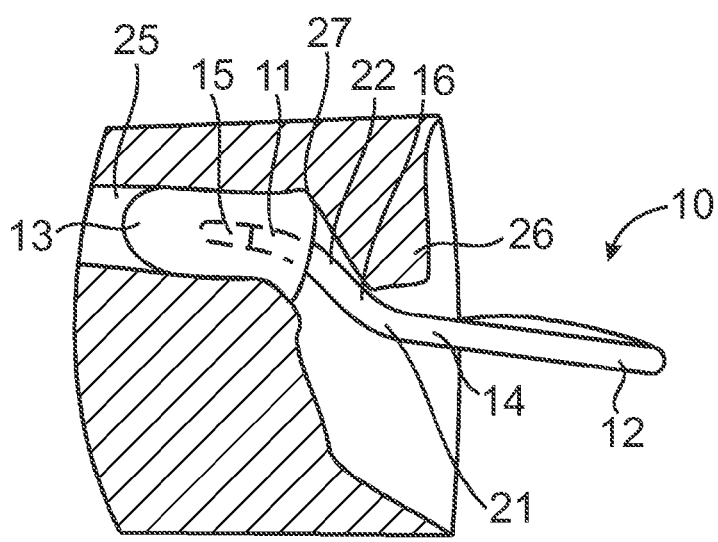

The invention will now be described more in detail with the aid of embodiments and with reference to the appended drawings, in which FIG. 1 is a schematic side view of a device for hearing protection according to one embodiment of the present invention, in which the device is provided with an earplug, FIG. 2 is a schematic view according to FIG. 1, in which the earplug has been removed, FIG. 3 is a schematic view from above of the device according to FIG. 2, FIG. 4 is a schematic view according to FIG. 3, FIG. 5 is a schematic view of the device seen along the stem according to one embodiment of the invention, FIG. 6 is a schematic cross section view along the line II-II in FIG. 4, FIG. 7 is a schematic view of an earplug according to one embodiment of the present invention seen from behind in an axial direction, FIG. 8 is a schematic view from above of the device according to one embodiment of the invention, FIG. 9 is a schematic cross section view along the line III-III in FIG. 8, FIG. 10 is a schematic view of an ear canal seen from behind and an earplug inserted into the ear canal according to one embodiment of the invention, and FIGS. 11-13 are a series of schematic views of an ear canal seen from above, in which the insertion of an earplug is illustrated according to one embodiment of the invention.

THE INVENTION

Referring to FIG. 1 and FIG. 2 a device 10 for hearing protection is illustrated schematically. In FIG. 1 and FIG. 2 a left-hand device 10L for use in a left ear and a right-hand device 10R for use in a right ear is illustrated. The left-hand device 10L is mirror-inverted in relation to the right-hand device 10R.

The device 10 comprises an elongated stem 11 and a grip part 12. The stem 11 and the grip part 12 are, for example, formed in one piece in a suitable plastic material. For example, the grip part 12 is marked to identify whether the device 10 is intended for use in a left ear or right ear.

According to FIG. 1 the stem 11 is connected to an earplug 13 for insertion into an ear canal, which is described in more detail below. According to one embodiment of the invention the earplug is detachable and replaceable. Alternatively, the earplug 13 is fixed to the stem 11. For example, the earplug 13 is arranged as one or more flanges projecting radially from the stem 11. The earplug 13 is, for example, arranged in a flexible material, such as foamed plastic or any other suitable plastic or rubber material.

The stem 11 comprises a connecting portion 14 for connection with the grip part 12, an attachment portion 15 for attachment to the earplug 13 and an intermediate portion 16 arranged between the connecting portion 14 and the attachment portion 15. For example, the stem 11 is arranged somewhat tapered in a direction towards the attachment portion 15. According to the illustrated embodiment the attachment portion 15 is provided with at least one radially projecting projection 17 for interaction with the earplug, so that the earplug 13 is retained at the attachment portion 15 of the stem 11. In the illustrated embodiment the attachment portion 15 is provided with a first projection 17a projecting in a first direction and a second projection 17b projecting in the opposite direction. For example, the projections 17a, 17b project in opposite directions in a vertical plane during use of the device 10. According to one alternative embodiment the attachment portion 15 is provided with further projections, such as perpendicular to the first projection 17a and the second projection 17b projecting projections, which are not illustrated in the drawings.

The grip part 12 is arranged to be held between the thumb and index finger of a user. In the illustrated embodiment the grip part 12 is arranged as a plate extending substantially in a first plane. For example, the first plane extends substantially in a vertical plane. For example, the grip part 12 extends in the same direction as the first projection 17a and the second projection 17b of the attachment portion 15. The grip part 12 is, in the illustrated embodiment, provided with a concave contact surface 18 for contacting the thumb of a user. For example, the grip part 12 is provided with a convex contact surface for contacting the index finger of a user, wherein the convex contact surface is arranged on the opposite side of the grip part 12 as the concave contact surface 18. For example, the concave contact surface 18 is marked to identify if the device 10 is intended for use in a left ear or right ear.

The grip part 12 is arranged in an angle to the stem 11, so that a centre axis A of the grip part 12 is arranged in an angle α to a centre axis B of the stem 11 at the connecting portion 14. The angle α is arranged in the plane of the grip part 12, i.e. the first plane, wherein the stem 11 projects obliquely upwards from the grip part 12 during use. The angle α corresponds substantially to an angle with which a normal ear canal is inclined. Hence, the angle α is more than 90° and for example 100°-150°, rather 105°-140°, 110°-130°, 115°-125°, 115°-120° or about 117°-118°.

In the illustrated embodiment the earplug 13 is arranged with a rounded top 19 and a wider base 20. Alternatively, the earplug is cylindrical.

Referring to FIG. 3 and FIG. 4 the stem 11 and the grip part 12 are illustrated more in detail. The stem 11 is arranged with a first curve 21 curving the stem 11 in a first direction and a second curve 22 curving the stem 11 in a second direction to incline the intermediate portion 16 forward and thereby facilitate insertion into an ear canal. The first curve 21 is arranged between the connecting portion 14 and the intermediate portion 16. The second curve 22 is arranged between the attachment portion 15 and the intermediate portion 16. The first curve 21 is arranged so that the intermediate portion 16 is inclined forward in relation to the connecting portion 14, wherein the intermediate portion 16 extends obliquely upward and forward in relation to the grip part 12 or the connecting portion 14 during use. The second curve 22 is, for example, arranged so that the attachment portion 15 extends substantially in parallel to the connecting portion 14 or the grip part 12. Hence, the stem 11 is arranged so that the attachment portion 15 is displaced in relation to the grip part 12 or the connecting portion 14. For example, the attachment portion 15 extends in a second plane being displaced in relation to the first plane, so that the attachment portion 15 is displaced forward in relation to the grip part 12 during use and so that the first projection 17a and the second projection 17b of the attachment portion 15 projects in the second plane. For example, the first plane is substantially in parallel to the second plane. Alternatively, the second plane is arranged in an angle to the first plane.

By means of the first curve 21 the intermediate portion 16 is arranged in a first angle β to the connecting portion 14 and, by means of the second curve 22, in a second angle γ to the attachment portion 15, so that the intermediate portion 16 is inclined backward in relation to the attachment portion 15 when the attachment portion 15 is connected to an earplug 13 arranged in an ear canal. The first angle β is arranged in a first direction and the second angle γ is arranged in a second direction opposite to the first direction. For example, the first angle β is more than 90°, so that the intermediate portion 16 is inclined forward in relation to the connecting portion 14. For example, the first angle β is 100-170°, 110-160°, 120-150°, 130-140° or about 135°. For example, the second angle γ corresponds to the first angle β, so that the attachment portion 15 is arranged substantially in parallel to the connecting portion 14. Alternatively, the attachment portion 15 is inclined in relation to the connecting portion 14. For example, the second angle γ is 100-170°, 110-160°, 120-150°, 130-140° or about 135°. Hence, the centre axis B of the stem 11 is curved so that the centre axis at the connecting portion 14 of the stem 11 is displaced radially in a lateral direction in relation to the centre axis B at the attachment portion 15 of the stem. For example, the lateral distance C between the centre axis B at the connecting portion 14 and the centre axis B at the attachment portion is 2-20 mm, 3-15 mm, 4-10 mm, 5-8 mm or about 6-7 mm. For example, the centre axis at the connecting portion 14 is arranged in the first plane, wherein the centre axis B at the attachment portion 15 is arranged in the second plane and wherein the second plane is arranged at the distance C from the first plane. The distance C extends between the first plane and the second plane. The first and second planes are arranged substantially vertical when the earplug is positioned in an ear canal, wherein the distance C extends substantially horizontally. The centre axis B of the attachment portion 15 is displaced in relation to the centre axis B of the connecting portion 14 both in horizontal and vertical direction.

For example, the grip part 12 is arranged with a length D of 5-30 mm or about 10-20 mm. The stem 11 is arranged with a length E from the grip part or a first end of the stem to the centre of the intermediate portion 16. Hence, the length E includes the connecting portion 14, the first curve 21 and half of the intermediate portion 16. Further, the stem 11 is arranged with a length F from the centre of the intermediate portion 16 to a second end of the stem 11. The length F includes half of the intermediate portion 16, the second curve 22 and the attachment portion 15. For example, the length E equals the length F. For example, the length E is 5-20 mm or about 10 mm, wherein the length F is 5-20 mm or about 10 mm. The total length of the stem 11 is, for example, 10-30 mm, 15-25 mm or about 20 mm. The total length of the stem 11 and the grip part 12 is, for example, 20-60 mm, 30-50 mm, 35-45 mm or about 40 mm.

Referring to FIG. 5 and FIG. 6 the design of the stem 11 according to one embodiment of the present invention is illustrated. The stem 11, or at least the attachment portion 15 of the stem 11, is arranged with an oval or elliptic cross section to prevent an earplug connected to the attachment portion 15 from turning around the centre axis B of the attachment portion 15. Hence, a cross section of the attachment portion 15 is arranged with a short axis X and a long axis Y. For example, the long axis Y extends substantially in the same direction as the first projection 17a and the second projection 17b and also in the same direction as the grip part 12. For example, the long axis Y, the first projection 17a, the second projection 17b and the grip part 12 extend substantially vertical when the device 10 is used.

Referring to FIG. 7 an earplug 13 according to one embodiment of the invention is illustrated. The earplug 13 is arranged with an oval or elliptic cross section corresponding to the attachment portion 15. Hence, a periphery or circumference of the earplug 13 is oval or elliptic to provide improved comfort and protection during use. In the illustrated embodiment, the earplug 13 is provided with a recess 23 for receiving the attachment portion 15, so that the attachment portion 15 can be inserted into the recess 23 to connect the earplug 13 with the stem 11. For example, the recess 24 is circular, elliptic, oval or provided with any suitable shape. In the embodiment in which the recess 23 is oval or elliptic the recess 23 extends in the same direction as the elliptic cross section of the earplug 13. Hence, when the earplug 13 is connected to the stem 11 a long axis of the earplug 13, and any long axis of the recess 23, is aligned with the long axis Y of the cross section of the attachment portion 15. Hence, the oval structure of the earplug 13 is aligned with the oval structure of the recess 23 and the attachment portion 15. The oval or elliptic shape of the earplug 13 extends substantially in the same direction as the grip part 12, i.e. substantially vertical during use.

With reference to FIG. 8 and FIG. 9 an alternative embodiment of the invention is illustrated, in which the attachment portion 15 is provided with a radially projecting flange 24 for interaction with the earplug 13 for connection therewith. The flange 24 is, for example, arranged at the second end of the stem 11. For example, the flange 24 extends around the periphery of the attachment portion 15.

Referring to FIG. 10 an ear canal 25 and the device according to one embodiment of the invention is schematically illustrated from behind. Seen from behind the ear canal 25 is inclined upward. To facilitate insertion of the earplug 13 the stem 11 is arranged at the angle α to the grip part 12, as described with reference to FIG. 2. During insertion of the earplug 13 in the ear canal 25 a user holds the grip part 12 between his thumb and index finger in such a way that the grip part 12 is directed substantially vertically downward, wherein the long axis of the oval or elliptic cross section of the earplug 13 extends in the same direction for correct positioning in relation to the ear canal 25. When the earplug 13 is inserted correctly the grip portion 12 is pointed downward.

Referring to FIG. 11 the ear canal 25 is illustrated from above. As disclosed in FIG. 11 the ear canal 25 is formed with a curvature due to tragus 26, so that a portion 28 of the ear canal 25 is inclined forward. During insertion of the earplug 13 in the ear canal 25 a user grip the grip part 12 and convey the stem 11 with the earplug 13 to the orifice of the ear canal. Then, the user angles the grip part 12 backward while bringing the stem 11 and the earplug 13 along therewith, so that the earplug can be brought into the curvature 27 of the ear canal 25 where tragus 26 is obstructive for further insertion into the ear canal 25, as illustrated in FIG. 12. Then, the grip part 12 is angled forward and can pass tragus 26 and the curvature 27 of the ear canal 25 to be in a comfortable and safe position in the ear canal 25, as illustrated in FIG. 13.

The invention claimed is:

1. A device for hearing protection, comprising an elongated stem and a grip part, wherein the stem comprises:
   a connecting portion for connection with the grip part,
   an attachment portion for attachment to an earplug projecting radially to the stem and being arranged for insertion into an ear canal,
   an intermediate portion arranged between the connecting portion and the attachment portion,
   a first curve arranged between the connecting portion and the intermediate portion, and
   a second curve arranged between the attachment portion and the intermediate portion,
   wherein the grip part has a longitudinal axis and the connecting portion has a longitudinal axis, the longitudinal axis of each of the grip part and the connecting portion being in a first plane, and the longitudinal axis of the connecting portion is arranged at an angle of greater than 90 degrees to the longitudinal axis of the grip part, and
   wherein the first and second curves are each greater than 90 degrees and complementary to each other so that the intermediate portion is arranged in a first angle to the connecting portion and a second angle to the attachment portion and so that a longitudinal axis of the attachment portion is in a part of a second plane that is offset from the first plane.

2. A device according to claim 1, wherein the attachment portion is connected to an earplug having oval cross section.

3. A device according to claim 2, wherein the grip part is formed as a plate extending in the first plane.

4. A device according to claim 2, wherein the attachment portion is oval in cross-section and wherein the earplug is formed with a recess for receiving the attachment portion.

5. A device according to claim 1, wherein the attachment portion is provided with at least one radially projecting projection for interaction with the earplug.

6. A device according to claim 1, wherein the stem is removably connectable to the earplug.

7. A device according to claim 1, wherein the longitudinal axis of the attachment portion extends substantially parallel to the longitudinal axis of the connecting portion.

8. A device according to claim 1, wherein first angle and the second angle is 100-170°, 110-160°, 120-150°, 130-140° or about 135°.

9. A device according to claim 1, wherein the angle between the connecting portion and the grip part is 100°-150°.

10. A device according to claim 1, wherein the device is arranged as a right-hand device for use in a right ear and for use together with a left-hand device for use in a left ear, the left-hand device being mirror-inverted in relation to the right-hand device.

11. A device according to claim 1, wherein the second plane is offset from and parallel to the first plane.

* * * * *